United States Patent [19]

Koinuma et al.

[11] Patent Number: 5,466,853

[45] Date of Patent: Nov. 14, 1995

[54] DIESTER MONOMER, ITS POLYMER, WATER-CONTAINING SOFT CONTACT LENS, AND PROCESSING SOLUTION FOR CONTACT LENS

[75] Inventors: Yasumi Koinuma; Takeo Matsumoto; Nobuharu Nakada, all of Tsukuba; Nobuo Nakabayashi, Matsudo; Kazuhiko Ishihara, Kodaira, all of Japan

[73] Assignee: NOF Corporation, Tokyo, Japan

[21] Appl. No.: 94,293

[22] Filed: Jul. 19, 1993

[30] Foreign Application Priority Data

| | | | |
|---|---|---|---|
| Jul. 23, 1992 | [JP] | Japan | 4-197235 |
| Jul. 23, 1992 | [JP] | Japan | 4-197236 |
| Jul. 23, 1992 | [JP] | Japan | 4-197237 |
| Jul. 23, 1992 | [JP] | Japan | 4-197238 |
| Jul. 24, 1992 | [JP] | Japan | 4-198633 |
| Jul. 24, 1992 | [JP] | Japan | 4-198634 |

[51] Int. Cl.$^6$ .................................... C07F 9/10
[52] U.S. Cl. ........................ 558/169; 558/158
[58] Field of Search ........................ 558/169, 158

[56] References Cited

FOREIGN PATENT DOCUMENTS 31786  2/1984  Japan .

OTHER PUBLICATIONS

Chem Abst, 116, 11,173y (1992).

*Primary Examiner*—Christopher Henderson
*Attorney, Agent, or Firm*—Darby & Darby

[57] ABSTRACT

A diester monomer is represented by the formula (I)

$$\begin{array}{c} H \\ \diagdown \\ R_1 \end{array} C=C \begin{array}{c} (CH_2)_m R_2 \\ \diagup \\ R_3 \end{array} \quad (I)$$

wherein $R_1$, $R_2$ and $R_3$ represent a hadrogen atom, an alkoxy, alkenyloxy or hydroxyalkyloxy carbonyl group having 1 to 20 carbon atoms, or a phosphorylcholine derivative $$-COO-(Y)-O-\overset{\overset{O}{\|}}{\underset{O^-}{P}}-O-CH_2-CH_2-N^+\diagup \begin{array}{c} R_4 \\ R_5 \\ R_6 \end{array}$$

where Y denotes $-(CH_2)_n$, $-(CH_2CH_2O)_nCH_2CH_2-$ $$-(CH_2\overset{\overset{CH_3}{|}}{CHO})_{\overline{n-1}}CH_2\overset{\overset{CH_3}{|}}{CH}-,$$

n denotes 1 to 8, m is an integer of 0 or 1, $R_4$, $R_5$ and $R_6$ denote an alkyl or aryl group having 1 to 8 carbon atoms, or a hydroxyalkyl group having 2 to 20 carbon atoms; on the proviso that if $R_1$ is a hydrogen atom, neither $R_2$ nor $R_3$ is a hydrogen atom and at least one of $R_2$ and $R_3$ denotes the aforesaid phosphorylcholine derivative group, and that if $R_2$ is a hydrogen atom, neither $R_1$ nor $R_3$ is a hydrogen atom and at least one of $R_1$ and $R_3$ denotes the aforesaid phosphorycholine derivative group. A polymer and a water-containing contact lens are obtained by polymerizing a starting component material including the above-mentioned diester monomer of the formula (I). A contact lens processing solution includes the polymer and a solvent for dissolving the polymer.

2 Claims, No Drawings

DIESTER MONOMER, ITS POLYMER, WATER-CONTAINING SOFT CONTACT LENS, AND PROCESSING SOLUTION FOR CONTACT LENS

BACKGROUND OF THE INVENTION

This invention relates to a polymer which may be utilized for a material for an artificial organ or a surface modifier for a high molecular material, a diester monomer employed as a starting monomer for the polymer, a water-containing soft contact lens, and a processing solution for the contact lens.

There have hitherto been known a variety of compounds, such as N-vinyl pyrrolidone, 2-hydroxy ethyl methacrylate or (meth)acrylic acid, as water-soluble monomers. Polymers obtained on polymerizing the water-soluble monomers are employed in bio-related fields, such as contact lenses or cosmetics. However, the aforementioned polymers suffer from drawbacks such as inferior mechanical strength or inadvertent adsorption of protein and lipid, such that these polymers are not satisfactory as a material directly related with a living tissue, such as a material for artificial organs.

Thus, a demand has been raised for a material having a functional relationship with a living body, and consequently a variety of monomers exhibiting biocompatibility have been proposed. As a monomer exhibiting biocompatibiity, 2-methacryl phosphorylcholine, which is a monomer having a structure similar to that of phospholipid, a main constituent of a membrane of a living body, has been proposed in Japanese Laid-open Patent Application No.54-63025 (1979). Attempts have been made for applying a polymer produced on polymerizing 2-methacryl phosphorylcholine to artificial organs, contact lenses or artificial blood vessels.

However, the above-mentioned 2-methacryl phosphorylcholine is susceptible to polymerization and poor in thermal stability because its polymerizable group is a methacrylic group. Besides, limitations are imposed on the kinds of comonomers which may be employed for copolymerization.

On the other hand, a water-containing soft contact lens has high affinity to an eye and may be fitted comfortably as compared to a non-water-containing hard contact lens containing methyl methacrylate or siloxanyl alkyl methacrylate as main monomer components.

As the water-containing soft contact lens, there has been known a contact lens which is composed mainly of 2-hydroxyethyl methacrylate and which, despite its moisture content of not higher than 40%, is superior in mechanical strength and machinability. Recently, a high water content soft contact lens has been developed with a view to continued attachment to the eye by raising the moisture content of the lens material. For example, there has been known a soft contact lens which is mainly composed of N-vinyl pyrrolidone copolymerized with methyl methacrylate, 2-hydroxyethyl methacrylate or methacrylic acid.

However, the soft contact lens composed mainly of N-vinyl pyrrolidone suffers from a number of drawbacks, such as susceptibility to deposition of dust and dirt, decreased mechanical strength, difficulties in lens processing by machining and grinding, and change to yellowish color caused by repetition of sterilization processes indispensable to soft contact lenses. On the other hand, although the soft contact lens composed mainly of 2-hydroxyethyl methacrylate, is free from these drawbacks, saturation of the lens with water takes much time because of the low water content of the lens, while the lens also suffers from production-related problems, such as fluctuations in the moisture content.

In general, a soft contact lens suffers from hygienic problems caused by deposition of protein and lipid or bacterial proliferation and a problem that a rise in the moisture content leads to a decreased mechanical strength. It is therefore usually necessary to maintain the contact lens in a sanitary condition by sterilization by boiling or treatment with a disinfectant or a rinsing solution.

The contact lens may be classified into a water-containing contact lens and a non-water-containing contact lens. The latter may be classified into a hard contact lens and a soft contact lens. The non-water-containing contact lens is superior to the water-containing contact lens in respect of stability of the lens material and ease in maintenance. There has so far been known such non-water-containing contact lens composed mainly of methyl methacrylate or formed of silicon rubber. Recently, a high oxygen permeable type hard contact lens composed mainly of silyl-based methacrylate or fluorine-based methacrylate for further reducing adverse effects on the eye, has been put to practical utilization.

However, the non-water-containing contact lens suffers from drawbacks that it has poor fitting feel because the lens surface exhibits hydrophobicity and the lens has adverse effects on the intraocular nerves. Above all, the high oxygen permeating hard contact lens exhibits strong hydrophobicity because of the content of a large quantity of silicon and fluorine, and hence is poor in tight fitting to the eye so that it is inferior in fitting feel and susceptible to deposition of protein or lipid.

For affording hydrophilicity to the hydrophobic surface of the contact lens, the contact lens is processed with plasma or with chemical substances, such as acidic or basic agents. However, such method suffers from a drawback that the lens surface can not be maintained in the hydrophilic condition with ease, while the contact lens tends to be modified by chemical processing and the processing operation tends to be complicated.

For affording hydrophilicity to the contact lens surface, it has also been proposed in Japanese Patent Publication No.48-37910 (1973) to dip the contact lens in a solution containing a water-soluble polymer, such as polyvinyl alcohol, hydroxyethyl cellulose or polyvinyl pyrrolidone or the like. However, this method has a drawback that limitations are imposed on the degree of hydrophilicity depending on the contact lens type, while it is impossible to prevent deposition of protein and lipid satisfactorily.

SUMMARY OF THE INVENTION

It is an object of the present invention to provide a diester monomer similar in structure to phospholipid exhibiting biocompatibility and a novel polymer which may be produced by polymerizing the monomer and which is superior in hydrophilicity, biocompatiblity and thermal stability.

It is another object of the present invention to provide a water-containing soft contact lens which has superior water content and high oxygen permeability, which may be improved in fitting feel with reduced adverse effects on the eye, and which may be fitted to the eye for a prolonged time with reduced amount of deposition of protein and lipid.

It is yet another object of the present invention to provide a solution for processing a contact lens whereby the non-water-containing contact lens surface may be improved in hydrophilicity by simple dipping, and the water-containing lens may be improved in its water content and whereby it is possible to suppress deposition and precipitation of protein or lipid on the lens.

The above and other objects of the invention will become apparent from the following description.

According to the present invention, there is provided a diester monomer represented by the formula (i)

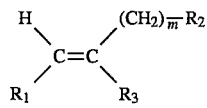  (I)

wherein $R_1$, $R_2$ and $R_3$ denote the same or different groups and represent a hydrogen atom, an alkoxy carbonyl group having 1 to 20 carbon atoms, an alkenyloxy carbonyl group having 1 to 20 carbon atoms or a hydroxyalkyloxy carbonyl group having 1 to 20 carbon atoms, or a phosphorylcholine derivative group of the formula

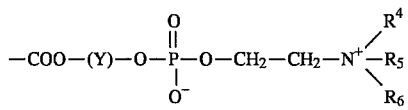

where Y denotes $-(CH_2)\overline{n}$, $-(CH_2CH_2O)_nCH_2CH_2-$ or

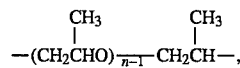, n denotes an integer of from 1 to 8, m is an integer of 0 or 1, $R_4$, $R_5$ and $R_6$ each denote an alkyl group having 1 to 8 carbon atoms, an aryl group having 1 to 8 carbon atoms or a hydroxyalkyl group having 2 to 20 carbon atoms; on the proviso that if $R_1$ is a hydrogen atom, neither $R_2$ nor $R_3$ is a hydrogen atom and at least one of $R_2$ and $R_3$ denotes the aforesaid phosphorylcholine derivative group, and that if $R_2$ is a hydrogen atom, neither $R_1$ nor $R_3$ is a hydrogen atom and at least one of $R_1$ and $R_3$ denotes the aforesaid phosphorylcholine derivative group.

According to the present invention, there is also provided a polymer with a number average molecular weight of 1000 to 500000, obtained by polymerizing a starting component material including the above-mentioned diester monomer represented by the formula (I).

According to the present invention, there is also provided a water-containing soft contact lens produced by polymerizing a starting component material including the above-mentioned diester monomer represented by the formula (I).

According to the present invention, there is also provided a contact lens processing solution containing, as essential components, the polymer produced by polymerizing the starting component material including the above-mentioned diester monomer represented by the formula (I) and a solvent for dissolving the polymer.

PREFERRED EMBODIMENTS OF THE INVENTION

The present invention will be explained in more detail hereinbelow.

The diester monomer of the present invention is represented by the formula

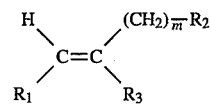  (I)

wherein $R_1$, $R_2$ and $R_3$ denote the same or different groups and represent a hydrogen atom, an alkyloxy carbonyl group having 1 to 20 carbon atoms, an alkenyloxy carbonyl group having 1 to 20 carbon atoms or a hydroxyalkyloxy carbonyl group having 1 to 20 carbon atoms, or a phosphorylcholine derivative group of the formula

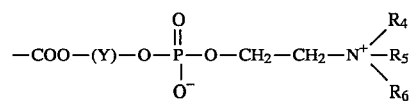

where Y denotes $-(CH_2)\overline{n}$, $-(CH_2CH_2O)_nCH_2CH_2-$ or

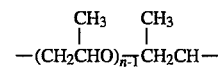

n denotes an integer of from 1 to 8, m is an integer of 0 or 1, $R_4$, $R_5$ and $R_6$ each denote an alkyl group having 1 to 8 carbon atoms, an aryl group having 1 to 8 carbon atoms or a hydroxyalkyl group having 2 to 20 carbon atoms; on the proviso that if $R_1$ is a hydrogen atom, neither $R_2$ nor $R_3$ is a hydrogen atom and at least one of $R_2$ and $R_3$ denotes

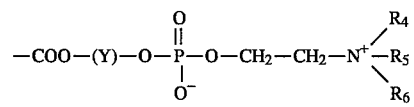

as aforesaid, and that if $R_2$ is a hydrogen atom, neither $R_1$ nor $R_3$ is a hydrogen atom and at least one of $R_1$ and $R_3$ denotes the aforesaid phosphorylcholine derivative group.

If, with the above-mentioned diester monomer, the number of carbon atoms of $R_1$, $R_2$ and $R_3$ exceeds 20, it becomes difficult to manufacture the monomer, whereas, if $R_4$, $R_5$ and $R_6$ are an alkyl or aryl group having 9 or more carbon atoms, or a hydroxyalkyl group having 21 or more carbon atoms, the monomer is lowered in hydrophilicity and polymerizability. On the other hand, if n exceeds 8, the polymer obtained by polymerization is lowered in thermal resistance and copolymerizability.

The diester monomer may be enumerated by, for example, α-methyl-β-((2'-trimethyl ammonio)ethyl ethyl phosphate) itaconate, β-methyl-α-((2'-trimethyl ammonio)ethyl ethyl phosphate)itaconate, α-ethyl-β-((2'-trimethyl ammonio) ethyl ethyl phosphate)itaconate, β-ethyl-α-((2'-trimethyl ammonio)ethyl ethyl phosphate)itaconate, α-propyl-β-((2'-trimethyl ammonio)ethyl ethyl phosphate)itaconate, β-propyl-α-((2'-trimethyl ammonio)ethyl ethyl phosphate)itaconate, α-sec-butyl-β-((2'-trimethyl ammonio)ethyl propyl phosphate)itaconate, α-n-hexyl-β-((2'-trimethyl ammonio)ethyl butyl phosphate)itaconate, α-(2"-hydroxyethyl)-β-((2'-trimethyl ammonio)ethyl ethyl phosphate)itaconate, β-(2"-hydroxyethyl)-α-((2'-trimethyl ammonio)ethyl ethyl phosphate)itaconate, α-(2"-hydroxyethyl)-β-((2'-trimethyl ammonio)ethyl propyl phosphate)itaconate, β-(2"-hydroxyethyl)-α-((2'-trimethyt ammonio)ethyl propyl phosphate)itaconate, α-ethyl-β-((2' -N,N-dimethyl-N-ethyl ammonio)ethyl ethyl phosphate)itaconate, α-(2"-hydroxyethyl)-β-((2'-N,N-dimethyl-N-ethyl ammonio)ethyl ethyl phosphate)itaconate, α-(2"-hydroxyethyl)-β-((2' -N,N-diethyl-N-methyl ammonio)ethyl ethyl phosphate)itaconate, β-ethyl-α-((2'-N,N-dimethyl-N-ethyl ammonio)ethyl ethyl phosphate)itaconate, α-ethyl-β-((2'-N,N-diethyl-N-methyl ammonio)ethyl ethyl phosphate)itaconate, β-ethyl-α-((2' -N,N-diethyl-N-methyl ammonio)ethyl ethyl phosphate)itaconate, α-ethyl-β-((2'-trimethyl ammonio)ethyl propyl phosphate) itaconate, β-ethyl-α-((2'-trimethyl ammonio)ethyl propyl phosphate)itaconate, α-ethyl-β-((2'-trimethyl ammonio)ethyl butyl phosphate)itaconate, β-ethyl-α-((2'-trimethyl ammonio) ethyl butyl phosphate)itaconate, α-ethyl-β-((2'-trimethyl ammonio)ethyl ethoxyethyl phosphate)itaconate, β-ethyl-α -((2'-trimethyl ammonio)ethyl ethoxyethyl phosphate)itaconate, α-ethyl-β-((2'-trimethyl ammonio)ethyl triethylene glycol phosphate)itaconate, α-ethyl-β-((2'-trimethyl ammonio)ethyl diisopropylene lycol phosphate)itaconate, β-ethyl-α-((2'-trimethyl ammonio)ethyl diisopropylene glycol phosphate)itaconate, α-ethyl-β-((2'-trimethyl ammonio)ethyl triethylene glycol phosphate)itaconate, βethyl-α-((2'-trimethyl ammonio)ethyl triethylene glycol phosphate)itaconate, α-ethyl-β-((2'-triethyl ammonio)ethyl ethyl phosphate)itaconate, α-isopropyl-β-((2'-tributyl ammonio)ethyl propyl phosphate)itaconate, α-methyl-β-((2'-trimethyl ammonio)ethyl hexyl phosphate)itaconate, α-myristyl-β-((2'-triphenyl ammonio)ethyl ethyl phosphate)itaconate, α-t-butyl-β-((2'-tri-2-hydroxyethyl ammonio)ethyl ethyl phosphate)itaconate, α-ethyl-β-((2'-trimethyl ammonio)ethyl ethoxyethyl phosphate)itaconate, α-allyl-β-((2'-trimethyl ammonio)ethyl ethyl phosphate)itaconate, α-hydroxyethyl-β-((2'-trimethyl ammonio)ethyl ethoxyethyl phosphate)itaconate, ethyl-((2'-trimethyl ammonio)ethyl ethyl phosphate)fumarate, isopropyl-((2'-trimethyl ammonio)ethyl ethyl phosphate)fumarate, t-butyl-((2'-trimethyl ammonio)ethyl ethyl phosphate)fumarate, cyclohexyl-((2'-trimethyl ammonio)ethyl ethyl phosphate)fumarate, 2-hydroxyethyl-((2'-trimethyl ammonio)ethyl ethyl phosphate)fumarate, isopropyl-((2'-triethyl ammonio)ethyl ethyl phosphate)fumarate, sec-butyl-((2'-N, N-diethyl-N-methyl ammonio)ethyl ethyl phosphate)fumarate, ethyl-((2'-trimethyl ammonio)ethyl propyl phosphate)fumarate, isopropyl-((2'-trimethyl ammonio)ethyl butyl phosphate)fumarate, isopropyl((2'-trimethyl ammonio)ethyl ethoxyethyl phosphate)fumarate, t-butyl-((2'-triethyl ammonio)ethyl ethoxyethyl phosphate)fumarate, isopropyl-((2'-trihydroxyethyl ammonio)ethyl ethyl phosphate)fumarate, cyclohexyl-((2'-triethyl ammonio)ethyl ethyl phosphate)fumarate, isopropyl-((2'-trimethyl ammonio) ethyl propyl phosphate)fumarate, sec-butyl-((2'-trimethyl ammonio)ethyl butyl phosphate)fumarate, allyl-((2'-trimethyl ammonio)ethyl butyl phosphate)fumarate, isopropyl-((2'-triethyl ammonio)ethyl ethyl phosphate)fumarate, cyclohexyl-((2'-tributyl ammonio)ethyl ethyl phosphate)fumarate, t-butyl-((2'-tri-2"-hydroxyethyl ammonio)ethyl ethyl phosphate)fumarate, di(2-trimethyl ammonio ethyl ethyl phosphate)fumarate, phenyl-((2'-trimethyl ammonio)ethyl ethyl phosphate)fumarate, hydroxyethyl-((2'-trimethyl ammonio)ethyl isopropoxy isopropyl phosphate)fumarate, ethyl-((2'-trimethyl ammonio)ethyl ethyl phosphate)maleate, isopropyl-((2' -trimethyl ammonio)ethyl ethyl phosphate)maleate, t-butyl-((2'-trimethyl ammonio)ethyl ethyl phosphate)maleate, cyclohexyl-((2'-trimethyl ammonio)ethyl ethyl phosphate)maleate, 2-hydroxyethyl-((2'-trimethyl ammonio)ethyl ethyl phosphate)maleate, isopropyl-((2'-triethyl ammonio)ethyl ethyl phosphate)maleate, sec-butyl-((2'-N,N-diethyl-N-methyl ammonio)ethyl ethyl phosphate)maleate, ethyl-((2'-trimethyl ammonio)ethyl propyl phosphate)maleate, isopropyl-((2'-trimethyl ammonio)ethyl butyl phosphate)maleate, isopropyl-((2'-trimethyl ammonio)ethyl ethoxyethyl phosphate)maleate, t-butyl-((2'-trimethyl ammonio)ethyl butyl phosphate)maleate, t-butyl-((2'-triethyl ammonio)ethyl ethoxyethyl phosphate)maleate, and isopropyl-((2'-trihydroxyethyl ammonio)ethyl ethyl phosphate)maleate.

The diester monomer may be prepared by a method consisting in reacting an itaconic acid derivative, such as α-alkyl-β-hydroxyethyl itaconate, a fumarate derivative, such as alkyl-hydroxyethyl fumarate, or a maleate derivative, and a phosphorane compound, such as 2-chloro-2-oxo-1,3,2-dioxaphosphorane or 2-bromoethyl phosphoryl dichloride, in the presence of a tertiary amine, such as trimethyl amine in a temperature range of from 0° to 50° C., for 1 to 20 hours, to produce a diester monophosphorane monomer, charging the resulting diester monophosphorane monomer, a hydrochloric acid removing agent, such as a tertiary amine, e.g. trialkyl amine or pyridine, and a solvent, such as acetonitrile in a pressure-resistant vessel, tightly sealing the vessel under a dry atmosphere, filtering at 50° to 60° C. and washing the resulting product with a cooled solvent. Alternatively, it may be prepared by a method consisting in reacting the above-mentioned diester monophosphorane monomer and the agent for removing hydrochloric acid at a reaction temperature of 20° to 100° C. for 1 to 48 hours. The charging molar ratio of the diester monophosphorane monomer, the hydrochloric acid removing agent and the solvent is preferably 1:1 to 10:1 to 20. The resulting product may be purified by any known method, such as recrystallization or column chromatography.

The polymer of the present invention, referred to hereinafter as polymer A, is a polymer obtained by polymerizing starting components containing the above-mentioned diester monomer. The number average molecular weight of the polymer A is 1000 to 500000 and preferably 2000 to 300000. If the molecular weight is outside the above range, it becomes difficult to produce the polymer.

There is no limitation to the polymer A if it contains the above-mentioned diester monomer units. It is possible to use any other copolymerizable vinyl monomer as a starting component.

Examples of these other copolymerizable vinyl monomers which may be employed in the polymer A of the present invention include monofunctional monomers, such as styrene, substituted methylstyrene, a-methylstyrene, substituted chlorostyrene, vinyl acetate, vinyl propionate, vinyl pivalate, methyl (meth)acrylate, ethyl (meth)acrylate, n-butyl (meth)acrylate, (meth)acrylic acid, (meth)acrylic acid amide, N,N-dimethyl (meth)acryl amide, 2-hydroxyethyl (meth)acrylate, vinyl pyridine, methylvinyl ether, ethylvinyl ether, n-butyl vinyl ether, N-vinyl pyrrolidone, diethyl itaconate, di-n-butyl itaconate, vinyl chloride, vinylidene chloride, ethylene, propylene, isobutylene or acrylonitrile; and polyfunctional monomers, such as allyl (meth)acrylate, ethylene glycol di(meth)acrylate, diethylene glycol di(meth)acrylate, triethylene glycol (meth)acrylate, tetraethylene glycol di(meth)acrylate, neopentyl glycol di(meth)acrylate, 1,4-butane diol di(meth)acrylate, di(meth)acrylate, diallyl phthalate, divinyl benzene, methylenebis acryl amide, diethylene glycolbis allyl carbonate, triallyl trimellitate, triallyl cyanurate or divinyl adipate. These may be used alone or in combination. The content of the aforementioned copolymerizable other vinyl monomer is preferably 1 to 10000 parts by weight to 100 parts by weight of the diester monomer if the aforementioned monofunctional monomer is employed. The content of the vinyl monomer in excess of 10000 parts by weight is not desirable because the polymer A is lowered in biocompatibility. The content of the vinyl monomer is used in an amount of not more than 20 parts by weight to 100 parts by weight of the diester monomer if the polyfunctional monomer is employed. In the latter case, a cross-linked polymer is produced.

The polymer A of the present invention may be easily produced by radical polymerization or copolymerization of the aforementioned diester monomer with or without the copolymerizable other vinyl monomer by any known methods of polymerization, such as block polymerization, suspension polymerization, solution polymerization or emulsion polymerization, in the presence of, e.g. a radical polymerization initiator. The radical polymerization initiator preferably includes benzoyl peroxide, lauroyl peroxide, diisopropyl peroxy dicarbonate, t-butyl peroxy-2-ethyl hexanoate, azobis (2,4-dimethyl valeronitrile), t-butyl peroxy pivalate, t-butyl peroxy-isobutylate, azobis isobutyronitrile, benzoin methyl ether, benzoin ethyl ether, persulfate or persulfate-hydrogen sulfite. The radical polymerization initiator is used in an amount of 0.01 to 10 parts by weight and preferably in an amount of 0.1 to 5 parts by weight to 100 parts by weight of the total starting monomer.

The polymerization reaction is preferably carried out by substituting inert gases, such as nitrogen, argon carbon dioxide or helium for the polymerization system, or under the atmosphere of these inert gases at a polymerization temperature of 20° to 140° C. for 5 to 120 hours. The polymer A with a narrower molecular weight distribution may be obtained by additionally carrying out a fractionating operation.

The water-containing soft contact lens according to the present invention is prepared by polymerizing a starting material containing the diester monomer represented by the formula (I) and preferably has a number average molecular weight of 1000 to 10000 and a moisture content of not less than 20% and particularly in a range of from 30 to 80%. That is, the soft contact lens is produced by copolymerizing the component of the starting material for polymer A, that is the above-mentioned diester monomer, and the other copolymerizable vinyl monomer.

The copolymerizable vinyl monomer, if used, is preferably 2000 to 1 parts by weight and more particularly 1000 to 5 parts by weight to 100 parts by weight of the diester monomer. If the vinyl monomer is used in an amount larger than 2000 parts by weight, the water-containing soft contact lens produced becomes significantly low in moisture content and thermal resistance, whereas if the vinyl monomer is used in an amount less than 1 part by weight, the effect proper to the vinyl monomer is not displayed.

For producing the water-containing soft contact lens, the above-mentioned starting components are admixed with a radical polymerization initiator, and the resulting mixture is charged into a vessel formed of metal, glass or plastics of a desired shape, such as a test tube or a lens, which vessel is then sealed tightly. The mixture in the vessel is polymerized under heat or light irradiation to produce a lens material or a lens-shaped product. The resulting product is machined and ground to form a contact lens, which is then swollen by hydration to produce a desired water-containing soft contact lens. It is also possible to employ a casting polymerization method for directly producing a lens or a method consisting in casting under light irradiation.

The radical polymerization initiator may be the same as that employed for the preparation of polymer A and may be used in similar amounts under similar polymerization conditions.

For polymerization, colorants such as dyestuffs, additives such as UV absorbers or other monomer components not affecting the functions proper to the lens may be added to the components of the starting material.

The contact lens processing solution according to the present invention contains a polymer produced by polymerizing the components of the starting material including the diester monomer of formula (I), that is the polymer A, and a solvent for dissolving the polymer A, as essential components.

The polymer contained in the contact lens processing solution according to the present invention as an essential component is substantially the same as the polymer A. However, if the other copolymerizable vinyl monomer is employed, such vinyl monomer is preferably employed in an amount of 5 to 10000 parts by weight to 100 parts by weight of the diester monomer. If the vinyl monomer is used in an amount exceeding 10000 parts by eight, solubility in water or resistance to contamination is not exhibited satisfactorily, whereas if the vinyl monomer is used in an amount less than 5 parts by weight, the effect proper to copolymerization is not displayed.

Although there is no particular limitation to the number average molecular weight of the polymer, depending on the polymerization temperature, the amount of the polymerization initiator or on whether or not a polymerization modifier is used, it is preferably in a range of from 1000 to 300000 and more preferably in a range of from 2000 to 20000 in view of the solubility into solvents later described, the viscosity of the contact lens processing solution and attachability to the contact lens surface. If the number average molecular weight is less than 1000, the solution is lowered in viscosity, whereas if it exceeds 300000, the solution is increased in viscosity to lower its operability.

The above-mentioned polymer may be produced by a method similar to the method for producing the polymer A.

There is no particular limitation to the solvent employed as an essential component in the contact lens processing solution according to the present invention, if it is capable of dissolving the polymer without exhibiting the effect of modifying or deforming the lens, and is miscible in water so as to afford hydrophilicity and resistance to pollution to the contact lens by a simplified operation of dipping and washing. Examples of such solvent include water, methanol, ethanol, isopropanol, ethylene lycol polyethylene glycol glycerin, ethylene glycol monomethyl ether, dimethyl sulfoxide, tetrahydrofuran and acetone. These may be used singly or in combination.

The mixing ratio of the polymer to the solvent in the contact lens processing solution according to the present invention is preferably so selected that the polymer accounts for 0.1 to 10 wt % based on the total weight of the processing solution. If the mixing ratio of the polymer is less than 0.01 wt %, hydrophilicity or resistance to pollution cannot be afforded sufficiently to the contact lens.

When using the contact lens processing solution according to the present invention, the processing solution is elevated in temperature preferably to 20° to 70° C., and the contact lens is dipped in or contacted with the processing solution. The contact lens is ready to be fitted to the eye on rinsing the contact lens with water, physiological saline or any other suitable rinsing solution.

Besides, the contact lens processing solution may be occasionally employed in conjunction with surfactants, disinfectants or antiseptics, and may also be employed as detergent or preservative.

The diester monomer of the present invention is a novel compound similar in structure to phospholipid, and is superior in radical polymerizability and in thermal stability. The polymer produced from such monomer exhibits hydrophilicity and biocompatibility and hence may be employed as a contact lens material or a material for artificial organs.

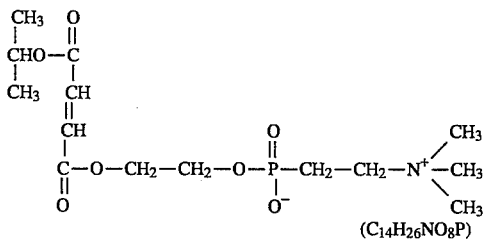

The water-containing soft contact lens according to the present invention is formed of a polymer of the above-mentioned monomer or a copolymer of the same polymer with other monomers and hence exhibits a high moisture ratio. Thus the soft contact lens is capable of furnishing oxygen to the cornea in an amount sufficient for maintaining physiological activity to improve the fitting feel to the eye. Besides, the soft contact lens is capable of suppressing deposition or precipitation of contaminants due to protein or lipid to improve safety to the eye as well as preventing the lens from being modified for obviating the defects of the conventional water-containing soft contact lens.

The contact lens processing solution according to the present invention contains the above-mentioned polymer as essential component and is capable of affording hydrophilicity and resistance to contamination due to protein or lipid by a simplified operation to improve the fitting feel to the eye as well as to prevent modification of the contact lens.

EXAMPLES OF THE INVENTION

Example 1-1

1 mol of a fumaric acid compound and 1.5 mol of an amine compound shown in Table 1-1 were charged in a reaction vessel along with 600 ml of acetonitrile as a solvent, and a ring-opening reaction was carried out in an autoclave under a nitrogen atmosphere for 15 hours. After completion of the reaction, the solution was filtered under a reduced pressure to recover an object product, which was then washed several times with acetonitrile to produce a crystalline product. The product was analyzed by elementary analysis and $^1$H-NMR and identified to be a fumaric acid diester monomer represented by the formula:

| | Elementary Analysis: | | |
|---|---|---|---|
| | C (%) | H (%) | N (%) |
| Calculated: | 45.78 | 7.08 | 3.82 |
| Found: | 45.80 | 7.05 | 3.77 |

| $^1$H-NMR (CDCL$_3$) σ(ppm) | |
|---|---|
| $-N-(CH_3)_3$ 3.3–3.4 | $-CH=CH-$ 6.8 |

Examples 1-2 to 1-6

A synthetic reaction was carried out in the same way as in Example 1-1 except using the starting materials shown in Table 1-1. Each of the resulting monomers was analyzed by elementary analysis and $^1$H-NMR.

Fumaric acid or maleic acid diester monomers produced are shown in Table 1-1.

TABLE 1-1

| | | | | Elementary Analysis | | | | |
|---|---|---|---|---|---|---|---|---|
| Ex. | Diester Compounds | Amine Compounds | Products | C | H | N | | $^1$H-NMR (ppm) |
| | | | | ( )Culculated Value | | | | |
| 1-1 | PODPEF | TMA | FPPC | 45.8 (45.78) | 7.05 (7.08) | 3.77 (3.82) | $-N^+(CH_3)_3$, 3.35 | $-CH=CH-$ 6.85 |
| 1-2 | PODPEF | TEA | FPPEC | 49.85 (49.88) | 7.78 (7.82) | 3.44 (3.42) | $-N^+(CH_3CH_3)_3$, 1.1~1.5 | $-CH=CH-$ 6.86 |
| 1-3 | EODPEF | TMA | FEPC | 45.78 (45.77) | 7.11 (7.08) | 3.85 (3.81) | $-N^+(CH_3)_3$, 3.30 | $-CH=CH-$ 6.88 |
| 1-4 | PODPDEGF | TMA | FPDEC | 46.52 (46.71) | 7.32 (7.30) | 3.31 (3.41) | $-N^+(CH_3)_3$, 3.32 | $-CH=CH-$ 6.87 |

TABLE 1-1-continued

| Ex. | Diester Compounds | Amine Compounds | Products | Elementary Analysis C ( )Calculated Value | H | N | $^{1}$H-NMR (ppm) | |
|---|---|---|---|---|---|---|---|---|
| 1-5 | BODPBM | TMA | MBPC | 49.90 (49.88) | 7.88 (7.82) | 3.43 (3.44) | $-N^{+}(CH_3)_3$, 3.29 | $-CH=CH-$ 6.25 |
| 1-6 | PODPEF | TEOHA | FPPEA | 49.50 (49.39) | 7.62 (7.75) | 3.35 (3.39) | $-N^{+}(CH_3)_3$, 3.37 | $-CH=CH-$ 6.80 |

Abbreviations used in Table 1-1 stand for the following compounds:
PODPEF; isopropyl-(2'-oxo-1',3',2'-dioxaphosphoryl) ethyl fumarate

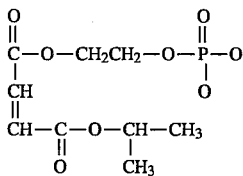

EODPEF; ethyl-(2'-oxo-1',3',2'-dioxaphosphoryl) ethyl fumarate
PODPDEGF; isopropyl-(2'-oxo-1',3',2'-dioxaphosphoryl) diethylglycol fumarate
BODPBM; t-butyl-(2'-oxo-1',3', 2'-dioxaphosphoryl) butyl maleate
TMA; trimethyl amine
TEA; triethyl amine
TEOHA; triethanol amine
FPPC; isopropyl-(2'-trimethyl ammonio ethyl ethyl phosphate) fumarate

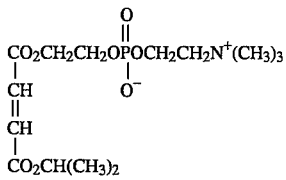

FPPEC; isopropyl-(2'-triethyl ammonio ethyl ethyl phosphate) fumarate
FEPC: ethyl-(2'-trimethyl ammonio ethyl propyl phosphate) fumarate
FPDEC; isopropyl-(2'-trimethyl ammonio ethyl ethoxyethyl phosphate) fumarate
MBPC; t-butyl-(2'-trimethyl ammonio ethyl butyl phosphate) maleate
FPPEA; isopropyl-(2'-trihydroxyethyl ammonio ethyl ethyl phosphate) fumarate

Example 1-7

To 10 g of isopropyl-(2'-trimethyl ammonio ethyl ethyl phosphate)maleate, there were add 40 ml of methanol containing azobis isobutyronitrile as a radical polymerization initiator at a rate of 20 mmol/l, and solution polymerization was carried out at 60° C. for 20 hours by a sealed tube method. After termination of polymerization, the polymer solution produced was charged into hexane and the precipitated polymer was filtered, washed and dried to find the degree of polymerization. Analyses of the resulting polymer by $^{1}$H-NMR have revealed that absorption by CH=CH as noticed in the monomer has disappeared so that the double bond has been cleaved. The molecular weight and other physical properties were measured by GPC measurement and by a transparent cast polymer film, respectively. The measurement methods are shown below, while the results of measurement are shown in Table 1-2.

a) Thermal Stability
Tests on thermal stability were conducted at 60° C. for 24 hours using a 1% aqueous solution of the monomer. Polymer samples showing no increase in viscosity were evaluated as ◯, while those showing rise in viscosity were evaluated as x.

b) Compatibility to Blood
Compatibility to blood was evaluated by a micro-sphere column method. Beads of acrylic resin coated with polymer samples were charged into a tube of polyvinyl chloride (diameter, 3 mm; length, 10 cm) into which a blood serum containing a large number of platelets was caused to flow by a syringe pump to measure the number of platelets flowing out.

Examples 1-8 to 1-16

Reaction was carried out in the same way as in Example 1-7 except using starting monomers shown in Table 1-2, and physical properties of the polymers produced were measured. The results are shown in Table 1-2.

Comparative Examples 1-1 to 1-4

Reaction was carried out in the same way as in Example 1-7 except using starting monomers shown in Table 1-2, and physical properties of the polymers produced were measured. The results are shown in Table 1-2.

TABLE 1-2

| Examples and Comparative Examples | Starting Monomers (g) | | Polymer Yield (%) | Number Average MW | Thermal Stability of Monomers | Compatibility to Blood (Platelet Flowing-out Percent, %) |
|---|---|---|---|---|---|---|
| Ex. 1-7 | FPPC | (10) | 85 | 31000 | O | 90 |
| Ex. 1-8 | FPEC | (10) | 76 | 28000 | O | 92 |
| Ex. 1-9 | FDEC | (10) | 74 | 26000 | O | 90 |
| Ex. 1-10 | FPPEA | (10) | 83 | 32000 | O | 94 |
| Ex. 1-11 | FPPC/VAc | (5/5) | 88 | 47000 | O | 88 |
| Ex. 1-12 | FEPC/VAc | (5/5) | 80 | 41000 | O | 90 |
| Ex. 1-13 | FEPC/St | (5/5) | 75 | 53000 | O | 86 |
| Ex. 1-14 | MBPC/VAc | (5/5) | 80 | 36000 | O | 91 |
| Ex. 1-15 | MBPC/St | (5/5) | 68 | 34000 | O | 85 |
| Ex. 1-16 | FPPEA/VAc | (5/5) | 84 | 44000 | O | 93 |
| Comp. Ex. 1-1 | HEMA | (10) | 94 | 74000 | x | 83 |
| Comp. Ex. 1-2 | NVP | (10) | 95 | 24000 | x | 72 |
| Comp. Ex. 1-3 | HEMA/St | (5/5) | 90 | 66000 | x | 65 |
| Comp. Ex. 1-4 | MPC/MMA | (5/5) | 80 | 34000 | x | 91 |

Abbreviations in Table 1-2 stand for the following compounds:
St; styrene
VAc; vinyl acetate
NVP; N-vinyl pyrrolidone
HEMA; 2-hydroxyethyl methacrylate
MPC; 2-methacryloyl phosphorylcholine
MMA; methyl methacrylate
The abbreviations not specified above are the same as those used in Table 1-1.

Example 2-1

Reaction was carried out in the same way as in Example 1-1 except using 1 mol of an itaconic acid compound shown in Table 2-1 and 1.5 mol of an amine compound shown in Table 2-1, and an itaconic acid diester monomer represented by the following formula was produced. The results of elementary analysis and $^1$H-NMR are as follows:

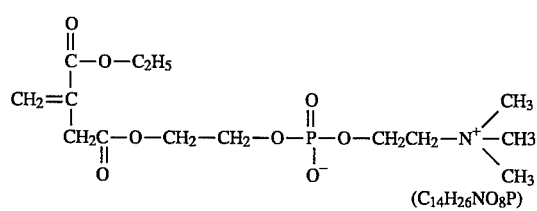

| Elementary Analysis: | | | |
|---|---|---|---|
| | C (%) | H (%) | N (%) |
| Calculated: | 45.6 | 7.1 | 3.8 |
| Found: | 45.8 | 7.0 | 4.1 |

| $^1$H-NMR(CDCL$_3$) σ(ppm) | |
|---|---|
| —N | —CH=CH< |
| 3.3~3.4 | 5.6~6.0 |

Examples 2-2 to 2-7

The synthetic reaction was carried out in the same way as in Example 2-1 except using the starting materials shown in Table 2-1, and each of the resulting monomers was analyzed by elementary analysis and $^1$H-NMR.

The resulting itaconic acid diester monomers and the results of analysis are shown in Table 2-1.

TABLE 2-1

| Ex. | Itaconic Acid Compounds | Amine Compounds | Products | Elementary Analysis | | | $^1$H-NMR (ppm) | |
|---|---|---|---|---|---|---|---|---|
| | | | | C | H | N | | |
| 2-1 | E-ODPEI | TMA | E-TMAEPEI | 45.8 | 7.0 | 4.1 | —N—(CH$_3$)$_3$ 3.3~3.4 | CH$_2$=C— 5.6~6.0 |
| 2-2 | HE-ODPEI | TMA | HE-TMAEPEI | 44.7 | 6.7 | 3.7 | —CH$_2$—CH$_2$OH 3.6~4.5 | |
| 2-3 | E-ODPPI | TMA | E-TMAEPPI | 47.3 | 7.2 | 3.9 | —CH$_2$CH$_3$ 1.4~1.6 | —N—(CH$_3$)$_3$ 3.3~3.4 |
| 2-4 | HE-ODPEI | DEMA | HE-DEMAEPEI | 48.3 | 7.5 | 3.5 | —CH$_2$—CH$_2$—OH 3.7~4.4 | N—CH$_3$ 1.1~1.4 |
| 2-5 | HE-ODPEI | DMEA | HE-DMEAEPEI | 46.7 | 7.2 | 3.5 | —CH$_2$—CH$_2$—OH 3.6~4.6 | |
| 2-6 | E-ODPDEGI | TMA | E-TMAEPDEGI | 46.4 | 7.1 | 3.3 | —(CH$_2$—CH$_2$—O)$_2$— 3.5~4.7 | |

TABLE 2-1-continued

| Ex. | Itaconic Acid Compounds | Amine Compounds | Products | Elementary Analysis | | | $^1$H-NMR (ppm) |
|---|---|---|---|---|---|---|---|
| | | | | C | H | N | |
| 2-7 | E-ODPTEGI | TMA | E-TMAEPTEGI | 46.2 | 7.0 | 3.3 | —(CH$_2$—CH$_2$—O)$_3$— 3.4–4.8 |

Abbreviations in Table 2-1 stand for the following compounds:
E-ODPEI; α-ethyl-(2'-oxo-1',3',2'-dioxaphosphoryl)-β-ethyl itaconate
HE-ODPEI; α-(2''-hydroxyethyl)-(2'-oxo-1',3',2'-dioxaphosphoryl)-β-ethyl itaconate
E-ODPPI; α-ethyl-(2'-oxo-1',3',2'-dioxaphosphoryl)-β-propyl itaconate
E-ODPDEGI; α-ethyl-(2'-oxo-1',3',2'-dioxaphosphoryl)-β-diethylene glycol itaconate
E-ODPTEGI; α-ethyl-(2'-oxo-1',3',2'-dioxaphosphoryl)-β-triethylene glycol itaconate
TMA; trimethylamine
DEMA; N,N-diethyl-N-methyl amine
DMEA; N,N-dimethyl-N-ethyl amine
E-TMAEPEI; α-ethyl-β-((2'-trimethyl ammonia) ethyl ethyl phosphate) itaconate
HE-TMAEPEI; α-(2''-hydroxyethyl)-β-((2'-trimethyl ammonia) ethyl ethyl phosphate) itaconate
E-TMAEPPI; α-ethyl-β-((2'-trimethyl ammonia) ethyl propyl phosphate) itaconate
HE-DMEAEPEI; α-(2''-hydroxyethyl)-β-((2'-N,N-dimethyl-N-ethyl ammonia) ethyl ethyl phosphate) itaconate
HE-DEMAEPEI; α-(2''-hydroxyethyl)-β-((2'-N,N-diethyl-N-methyl ammonia) ethyl ethyl phosphate) itaconate
E-TMAEPDEGI; α-ethyl-β-((2'-(trimethyl) ammonia) ethyl diethylene glycol phosphate) itaconate
E-TMAEPTEGI; α-ethyl-β-((2'-(trimethyl) ammonia) ethyl triethylene glycol phosphate) itaconate

Example 2-8

A polymer sample was produced in the same way as in Example 1-7 except using 10 g of α-ethyl-β-(2'-trimethyl ammonio ethyl ethyl phosphate)itaconate in place of 10 g of isopropyl (2'-trimethyl ammonio ethyl ethyl phosphate) maleate. Analysis of the polymer by $^1$H-NMR has revealed that absorption by CH$_2$=C(5.6, 6.0 ppm) as noticed with the monomer has disappeared, thus indicating the cleavage of the double bonds. The molecular weight and other physical properties were measured in the same way as in Example 1-7 by GPC measurement and by using a transparent cast polymer film. The results are shown in Table 2-2.

Examples 2-9 to 2-17

Polymerization was carried out in the same way as in Example 2-8 except using the starting monomers shown in Table 2-2, and measurement was made of the physical properties of the produced polymer samples. The results are shown in Table 2-2.

a polymerization initiator was charged into a glass mold in the shape of a test tube. After the system was sufficiently replaced by nitrogen, the system was repeatedly evacuated and the mold was sealed for heating to cure the mixture. Heating was conducted in a constant temperature chamber from 40° C. to 120° C. over 50 hours. After termination of polymerization, the cured product was taken out as a transparent colorless polymer from the mold. The polymer was machined and ground in the usual manner to give a contact lens or a test piece having a desired shape. The following physical properties of the product were measured. Table 3-1 shows the components of the starting material and the measured results of the physical properties.

Water Content

The contact lens was swollen by being dipped in 0.9% physiological saline. The water content was then measured by the following formula:

Water Content (wt %)=(W1−W2)/W1×100 where W1 and W2 stand for the weight of the lens saturated

TABLE 2-2

| Examples | Starting Monomers (g) | | Polymer Yield (%) | Number Average MW | Thermal Stability of Monomers | Compatibility to Blood (Platelet Flowing-out Percent, %) |
|---|---|---|---|---|---|---|
| Ex. 2-8 | E-TMAEPEI | (10) | 85 | 22000 | ○ | 95 |
| Ex. 2-9 | HE-TMAEPEI | (10) | 81 | 30000 | ○ | 95 |
| Ex. 2-10 | E-TMAEPPI | (10) | 67 | 21000 | ○ | 90 |
| Ex. 2-11 | HE-DEMAEPEI | (10) | 84 | 27000 | ○ | 93 |
| Ex. 2-12 | HE-DMEAEPEI | (10) | 70 | 19000 | ○ | 92 |
| Ex. 2-13 | E-TMAEPTEGI | (10) | 74 | 31000 | ○ | 92 |
| Ex. 2-14 | E-TMAEPDEGI | (10) | 71 | 34000 | ○ | 91 |
| Ex. 2-15 | E-TMAEPEI/MMA | (5/5) | 89 | 64000 | ○ | 93 |
| Ex. 2-16 | HE-TMAEPEI/St | (5/5) | 70 | 28000 | ○ | 91 |
| Ex. 2-17 | E-TMAEPEI/VAc | (5/5) | 69 | 25000 | ○ | 83 |

Abbreviations in Table 2-2 are the same as those in Tables 1-2 and 2-1.

Example 3-1

A mixed solution composed of 19 g of α-isopropyl-β-((2'-trimethyl ammonio)ethyl ethyl phosphate)itaconate, 1 g of allyl methacrylate and 0.02 g of t-butylperoxy pivalate as with water and dry weight of the lens, respectively.

Oxygen Permeation Coefficient

The oxygen permeation coefficient was measured at 35° C. in a 0.9% physiological saline using "K-316 IPI TYPE FILM OXYGEN PERMEABILITY METER", film oxygen permeation tester (RIKA SEIKI KOGYO KK).

Resistance to Contamination

The contact lens was immersed at 35° C. for two weeks in a physiological saline solution containing 0.39 wt % of albumin, 0.17 wt % of lysozyme and 0.105 wt % of globulin.

The contact lens was then washed with physiological saline and protein was peeled from the contact lens using a surfactant. A reagent for protein quantitation, manufactured and sold by PIERS CO. under the trade name of "MICRO BCA PROTEIN ASSAY REAGENT", was infused into the solution for measuring the quantity of protein adsorbed to the contact lens.

Examples 3-2 to 3-5

Polymerization was carried out in the same way as in Example 3-1, except using various components of the starting material shown in Table 3-1, and the resulting products were processed and measured as to physical properties. The results are shown in Table 3-1.

Comparative Examples 3-1 and 3-2

Contact lenses were processed and evaluated as to physical properties thereof in the same way as in Example 3-1 except using 99 g of 2-hydroxy ethyl methacrylate and 1 g of ethylene glycol dimethacrylate (Comparative Example 3-1) or 55 g of 2-hydroxy ethyl methacrylate, 40 g of N-vinyl pyrrolidone and 5 g of ethylene glycol dimethacrylate (Comparative Example 3-2). The results are shown in Table 3-1.

TABLE 3-1

|  | Components of Starting Material (g) | | Water Content (wt. %) | Oxygen Permeation Coefficient* | Resistance to Contamination (μg/cm$^2$) |
|---|---|---|---|---|---|
| Ex. 3-1 | α-Isopropyl-β-((2'-Trimethyl Ammonia) Ethyl Ethyl Phosphate) Itaconate | (19) | 65 | 69 | 3.1 |
|  | Allyl Methacrylate | (1) | | | |
| Ex. 3-2 | α-Ethyl-β-((2'-Trimethyl Ammonia) Ethyl Butyl Phosphate) Itaconate | (10) | 75 | 72 | 2.3 |
|  | 2-Hydroxyethyl Methacrylate | (10) | | | |
| Ex. 3-3 | α-Butyl-β-((2'-Trimethyl Ammonia) Ethyl Ethyl Phosphate) Itaconate | (5) | 53 | 37 | 3.4 |
|  | 2-Hydroxyethyl Methacrylate | (14) | | | |
|  | Ethylene Glycol Dimethacrylate | (1) | | | |
| Ex. 3-4 | α-Myristyl-β-((2'-Trimethyl Ammonia) Ethyl Ethyl Phosphate) Itaconate | (5) | 45 | 32 | 3.1 |
|  | 2-Hydroxyethyl Methacrylate | (14) | | | |
|  | Ethylene Glycol Dimethacrylate | (1) | | | |
| Ex. 3-5 | α-Ethyl-β-((2'-Trimethyl Ammonia) Ethyl Propyl Phosphate) Itaconate | (5) | 77 | 75 | 2.1 |
|  | N-vinyl Pyrrolidone | (14) | | | |
|  | Ethylene Glycol Dimethacrylate | (1) | | | |
| Comp. Ex. 3-1 | 2-Hydroxyethyl Methacrylate | (99) | 36 | 12 | 5.1 |
|  | Ethylene Glycol Dimethacrylate | (1) | | | |
| Comp. Ex. 3-2 | 2-Hydroxyethyl Methacrylate | (55) | 70 | 68 | 4.3 |
|  | N-Vinyl Pyrrolidone | (40) | | | |
|  | Ethylene Glycol Dimethacrylate | (5) | | | |

*: ($\times 10^{-10}$ cc(STP) cm/cm$^2$ · sec · mmHg)

Example 4-1

A mixed solution composed of 50 of isopropyl ((2'-trimethyl ammonio)ethyl ethyl phosphate)fumarate, 50 g of 2-hydroxyethyl acrylate and 0.2 g of t-butylperoxy pivalate as a polymerization initiator was charged into a glass mold in the shape of a test tube. After the system was sufficiently replaced by nitrogen, the system was repeatedly evacuated and the mold was sealed for heating to cure the mixture. Heating was conducted in a constant temperature chamber from 40° C. to 120° C. over 50 hours. After termination of polymerization, the cured product was taken out as a transparent colorless polymer from the mold. The polymer was machined and ground in the usual manner to give a contact lens or a test piece having a desired shape. The following physical properties of the product were measured in the same way as in Example 3-1. Table 4-1 shows the components of the starting material and the measured results of the physical properties.

Examples 4-2 to 4-5

Polymerization was carried out in the same way as in Example 4-1, except using various components of the starting material shown in Table 4-1, and the resulting products were processed and measured as to physical properties. The results are shown in Table 4-1.

TABLE 4-1

| | Components of Starting Material | (g) | Water Content (wt. %) | Oxygen Permeation Coefficient* | Resistance to Contamination ($\mu g/cm^2$) |
|---|---|---|---|---|---|
| Ex. 4-1 | Isopropyl-β-((2'-Trimethyl Ammonia) Ethyl Ethyl Phosphate) Fumarate | (50) | 68 | 70 | 2.5 |
| | 2-Hydroxyethyl Acrylate | (50) | | | |
| Ex. 4-2 | t-Butyl-((2'-Trimethyl Ammonio)Ethyl Ethyl Phosphate) Fumarate | (20) | 52 | 32 | 3.0 |
| | 2-Hydroxyethyl Methacrylate | (80) | | | |
| Ex. 4-3 | Allyl-((2'-Trimethyl Ammonia) Ethyl Butyl Phosphate) Fumarate | (50) | 65 | 60 | 2.1 |
| | 2-Hydroxyethyl Acrylate | (48) | | | |
| | Diethylene Glycol Dimethacrylate | (2) | | | |
| Ex. 4-4 | Cyclohexyl-((2'-Triethyl Ammonia) Ethyl Ethyl Phosphate) Fumarate | (50) | 62 | 47 | 3.3 |
| | Vinyl Acetate | (48) | | | |
| | Diallyl Phthalate | (2) | | | |
| Ex. 4-5 | Isopropyl-((2'-Triethyl Ammonia) Ethyl Ethyl Phosphate) Fumarate | (50) | 73 | 74 | 2.0 |
| | N-vinyl Pyrrolidone | (48) | | | |
| | Ethylenebis Acrylamide | (2) | | | |

*: ($\times 10^{-10}$ cc(STP) cm/cm² · sec · cmHg)

Example 5-1

(A) Preparation of Contact Lens Processing Solution 5 g of α-isopropyl-β-((2'-trimethyl ammonio)ethyl ethyl phosphate)itaconate, 5 g of methyl methacrylate and 0.1 g of azobis isobutyronitrile were dissolved in 30 g of ethanol and sealed in a glass tube. After nitrogen substitution, the glass tube was sealed and the starting monomers in the glass tube were polymerized at 60° C. for 12 hours to produce a polymer. The polymer produced was reprecipitated and purified, using 100 g of ethanol/diethyl ether (3/7), and dried. 2 g of the resulting dried mass were dissolved in 98 g of ethylene lycol to produce a contact lens processing solution.

(B) Preparation of Contact Lens Test Piece

On the other hand, the following three test pieces of the contact lenses were prepared.

(1) Hard contact lens 99 g of methyl methacrylate, 1 g of diethylene glycol dimethacrylate and 0.2 g of azobis isobutyronitrile were charged into a glass tube. After repeated nitrogen substitution and evacuation, the glass tube was sealed and the temperature was raised from 30° C. to 100° C. over 50 hours for heating and curing the starting monomers in the glass tube to produce a colorless transparent polymer. The polymer produced was machined and ground in the usual manner to produce a contact lens test piece having a desired shape.

(2) Oxygen Permeable Hard Contact Lens

A test piece was prepared in the same way as for producing the hard contact lens (1) except using 40 g of tris(trimethylsiloxy)silyl propyl methacrylate, 30 g of trifluoroethyl methacrylate, 10 g of methyl methacrylate, 15 g of triethylene glycol dimethacrylate and 5 g of methacrylic acid.

(3) Soft Contact Lens

A test piece was prepared in the same way as for producing the hard contact lens (1) except using 99 g of 2-hydroxyethyl methacrylate and 1 g of ethylene glycol dimethacrylate.

(C) Measurement of Hydrophilicity and resistance to Contamination of Contact Lens Processing Solution A contact lens storage casing was filled with the contact lens processing solution in which the contact lens test pieces (1) to (3) were immersed for 30 minutes. The test pieces were subsequently washed with water and hydrophilicity and resistance to contamination thereof were measured by the following methods. The results are shown in Table 5-1.

a) Measurement of Hydrophilicity

After drying the test piece surface, water contact angles of the test piece surface were measured by a water droplet method, in which the smaller the contact angle, the higher is the hydrophilicity of the test pieces.

(b) Measurement of Resistance to Contamination

The test pieces were immersed at 35° C. for two weeks in a physiological saline solution containing 0.39 wt % of albumin, 0.17 wt % of lysozyme and 0.105 wt % of globulin. The test pieces were then taken out from the saline and washed with physiological saline and freed of protein using a surfactant. A reagent for protein quantitation, manufactured and sold by PIERS CO. under the trade name of "MICRO BCA PROTEIN ASSAY REAGENT", was infused into the solution for measuring the quantity of protein adsorbed to the test pieces.

Example 5-2

A contact lens processing solution as prepared in the same way as in Example 5-1 except using, as starting monomers, 5 of α-n-hexyl-β-((2'-trimethyl ammonio)ethyl butyl phosphate)itaconate, 5 g of methyl methacrylate and 98 g of ethylene glycol as a solvent, and hydrophilicity and resistance to contamination of the produced processing solution were measured in respect of each of the test pieces. The results are shown in Table 5-1.

Example 5-3

A contact lens processing solution was prepared in the same way as in Example 5-1 except using, as starting monomers, 9 g of α-ethyl-β-((2'-tri-2"-hydroxyethyl ammonio)ethyl ethyl phosphate)itaconate, 1 g of styrene and 98 g of ethylene glycol/water (50/50) as a solvent, and hydrophilicity and resistance to contamination of the produced processing solution were measured in respect of each of the test pieces. The results are shown in Table 5-1.

Comparative Example 5-1

The hard contact lens (1) prepared in Example 5-1 was processed in the same way as in Example 5-1 except using 100 g of an aqueous solution of polyvinyl alcohol (saponification degree, 88%) and measurement was made of hydrophilicity and resistance to contamination of the test piece. The results are shown in Table 5-1.

Comparative Example 5-2

Measurements were made of hydrophilicity and resistance to contamination of the oxygen permeating hard contact lens (2) prepared in Example 5-1 without any processing. The results of measurement are shown in Table 5-1.

TABLE 5-1

| Examples and Comparative Examples | Contact Lens Test Piece* | Contact Angle (Degrees) | Protein Concentration (μg/cm$^2$) |
| --- | --- | --- | --- |
| Ex. 5-1 | (1) | 55.3 | 4.4 |
|  | (2) | 50.1 | 3.5 |
|  | (3) | 48.7 | 3.4 |
| Ex. 5-2 | (1) | 54.3 | 3.2 |
|  | (2) | 55.8 | 4.0 |
|  | (3) | 49.3 | 3.2 |
| Ex. 5-3 | (1) | 49.5 | 3.5 |
|  | (2) | 52.1 | 3.2 |
|  | (3) | 50.5 | 3.0 |
| Comp. Ex. 5-1 | (1) | 78.3 | 9.2 |
| Comp. Ex. 5-2 | (2) | 92.5 | 9.6 |

*) The numbers in parentheses stand for the following:
(1) hard contact lens
(2) oxygen permeating hard contact lens
(3) soft contact lens Example 6-1

Preparation of Contact Lens Processing Solution 5 g of isopropyl-((2'-trimethyl ammonio)ethyl ethyl phosphate)fumarate, 5 g of vinyl acetate and 0.1 of azobis isobutyronitrile were dissolved in 30 g of ethanol and sealed in a glass tube After nitrogen substitution, the glass tube was sealed and the starting monomer in the glass tube was polymerized at 60° C. for 12 hours to produce a polymer. The polymer produced was reprecipitated and purified, using 100 g of ethanol/ diethyl ether (3/7) and dried. 2 of the resulting dried mass were dissolved in 98 g of ethylene glycol to produce a contact lens processing solution.

Measurement of Hydrophilicity and Resistance to Contamination of Contact Lens Processing Solution A contact lens storage casing was filled with the contact lens processing solution in which the contact lens test pieces (1) to (3) prepared in Example 5-1 were immersed for 30 minutes. The test pieces were subsequently washed with water and hydrophilicity and resistance to contamination thereof were measured in the same way as in Example 5-1. The results are shown in Table 6-1.

Example 6-2

A contact lens processing solution was prepared in the same way as in Example 6-1, except using, as starting monomers, 9 g of isopropyl-((2'-trimethyl ammonio)ethyl ethyl phosphate)fumarate, 1 g of styrene and 98 g of ethylene glycol/water (50/50) as a solvent, and hydrophilicity and resistance to contamination thereof were measured in respect of each of the test pieces. The results of measurement are shown in Table 6-1.

Example 6-3

A contact lens processing solution was prepared in the same way as in Example 6-1, except using, as starting monomers, 5 g of t-butyl-((2'-tributyl ammonio)ethyl ethyl phosphate)fumarate, 5 g of vinyl acetate and 98 g of ethyleneglycol as a solvent, and hydrophilicity and resistance to contamination thereof were measured in respect of each of the test pieces. The results of measurement are shown in Table 6 -1.

TABLE 6-1

| Examples | Contact Lens Test Piece * | Contact Angle (Degrees) | Protein Concentration (μg/cm$^2$) |
| --- | --- | --- | --- |
| Ex. 6-1 | (1) | 48.3 | 3.5 |
|  | (2) | 49.8 | 3.2 |
|  | (3) | 48.2 | 3.0 |
| Ex. 6-2 | (1) | 51.0 | 4.8 |
|  | (2) | 50.5 | 4.7 |
|  | (3) | 47.3 | 4.5 |
| Ex. 6-3 | (1) | 52.1 | 4.0 |
|  | (2) | 50.5 | 3.2 |
|  | (3) | 48.5 | 2.8 |

*) The numbers in parentheses stand for the following:
(1) hard contact lens
(2) oxygen permeating hard contact lens
(3) soft contact lens Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. An itaconate diester monomer having a phosphorylcholine derivative group represented by the formula (I)

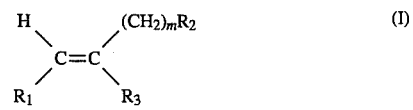

wherein $R_1$, represents a hydrogen atom, and $R_2$ and $R_3$ denote the same or different groups and represent an alkoxy carbonyl group having 1 to 20 carbon atoms, an alkenyloxy carbonyl group having 1 to 20 carbon atoms or a hydroxyalkyloxy phosphorylcholine derivative group of the formula

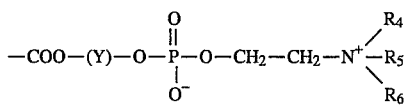

wherein Y denotes $-(CH_2)_n$, $-(CH_2CH_2O)_nCH_2CH_2-$ or

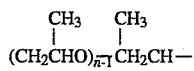

n denotes an integer of from 1 to 8, m is an integer of 1, $R_4$, $R_5$ and $R_6$ each denote an alkyl group having 1 to 8 carbon atoms, an aryl group having 1 to 8 carbon atoms or a hydroxyalkyl group having 2 to 20 carbon atoms; on the proviso that at least one of $R_2$ and $R_3$ denotes

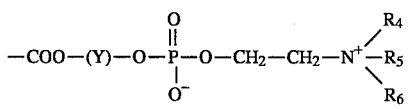

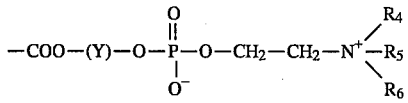

as given above.

2. The diester monomer as claimed in claim 1 wherein the diester monomer is selected from the group consisting of α-methyl-β-((2'-trimethyl ammonio)ethyl ethyl phosphate)itaconate, β-methyl-α-((2'-trimethyl ammonio)ethyl ethyl phosphate)itaconate, α-ethyl-β-((2'-trimethyl ammonio)ethyl ethyl phosphate) itaconate, β-ethyl-α-((2'-trimethyl ammonio)ethyl ethyl phosphate)itaconate, α-propyl-β-((2'-trimethyl ammonio)ethyl ethyl phosphate)itaconate, β-propyl-α-((2'-trimethyl ammonio)ethyl ethyl phosphate)itaconate, α-sec-butyl-β((2'-trimethyl ammonio)ethyl propyl phosphate)itaconate, α-n-hexyl-β-((2'-trimethyl ammonio) ethyl butyl phosphate)itaconate, α-(2"-hydroxyethyl)-β-((2'-trimethyl ammonio)ethyl ethyl phosphate)itaconate, β-(2"-hydroxyethyl)-α-((2'-trimethyl ammonio)ethyl ethyl phosphate)itaconate, α-(2"-hydroxyethyl)-β-((2'-trimethyl ammonio)ethyl propyl phosphate)itaconate, β-(2"-hydroxyethyl)-α-((2'-trimethyl ammonio)ethyl propyl phosphate)itaconate, α-ethyl-β-((2'-N,N-dimethyl-N-ethyl ammonio)ethyl ethyl phosphate)itaconate, α-(2"-hydroxyethyl)-β-((2'-N,N-dimethyl-N-ethyl ammonio) ethyl ethyl phosphate)itaconate, α-(2"-hydroxyethyl)-β-((2'-N,N-diethyl-N-methyl ammonio)ethyl ethyl phosphate)itaconate, β-ethyl-α-((2'-N,N-dimethyl-N-ethyl ammonio)ethyl ethyl phosphate)itaconate, α-ethyl-β-((2'-N,N-diethyl-N-methyl ammonio)ethyl ethyl phosphate)itaconate, β-ethyl-α-((2'-N,N-diethyl-N-methyl ammonio)ethyl ethyl phosphate)itaconate, α-ethyl-β-((2'-trimethyl ammonio)ethyl propyl phosphate)itaconate, β-ethyl-α-((2'-trimethyl ammonio)ethyl propyl phosphate)itaconate, α-ethyl-β-((2'-trimethyl ammonio)ethyl butyl phosphate) itaconate, β-ethyl-α-((2'-trimethyl ammonio ethyl butyl phosphate)itaconate, α-ethyl-β-((2'-trimethyl ammonio)ethyl ethoxyethyl phosphate)itaconate, β-ethyl-α-((2'-trimethyl ammonio)ethyl ethoxyethyl phosphate)itaconate, α-ethyl-β-((2'-trimethyl ammonio)ethyl triethylene glycol phosphate)itaconate, α-ethyl-β-((2'-trimethyl ammonio)ethyl diisopropylene glycol phosphate)itaconate, β-ethyl-α-((2'-trimethyl ammonio)ethyl diisopropylene glycol phosphate)itaconate, α-ethyl-β-((2'-trimethyl ammonio)ethyl triethylene glycol phosphate)itaconate, β-ethyl-α-((2'-trimethyl ammonio)ethyl triethylene glycol phosphate)itaconate, α-ethyl-β-((2'-triethyl ammonio)ethyl ethyl phosphate)itaconate, α-isopropyl-β-((2'-tributyl ammonio)ethyl propyl phosphate)itaconate, α-methyl-β-((2'-trimethyl ammonio)ethyl hexyl phosphate)itaconate, α-myristyl-β-((2'-triphenyl ammonio)ethyl ethyl phosphate) itaconate, α-t-butyl-β-((2'-tri-2"-hydroxyethyl ammonio)ethyl ethyl phosphate) itaconate, α-ethyl-β-((2"-trimethyl ammonio)ethyl ethoxyethyl phosphate)itaconate, α-allyl-β-((2'-trimethyl ammonio)ethyl ethyl phosphate)itaconate, and α-hydroxyethyl-β -((2'-trimethyl ammonio)ethyl ethoxyethyl phosphate)itaconate.

* * * * *